US010881460B2

(12) United States Patent
Åkesson

(10) Patent No.: US 10,881,460 B2
(45) Date of Patent: Jan. 5, 2021

(54) MEDICAL DEVICE FOR TREATMENT OF DEFECTIVE BLOOD VESSELS, BODY CAVITIES, AND BODY DUCTS

(71) Applicant: MedVASC AB, Malmö (SE)

(72) Inventor: Michael Åkesson, Höllviken (SE)

(73) Assignee: MedV ASC AB, Malmö (SE)

(*) Notice: Subject to any disclaimer, the term of this patent is extended or adjusted under 35 U.S.C. 154(b) by 417 days.

(21) Appl. No.: 15/526,945

(22) PCT Filed: Nov. 17, 2015

(86) PCT No.: PCT/SE2015/051234
§ 371 (c)(1),
(2) Date: May 15, 2017

(87) PCT Pub. No.: WO2016/080896
PCT Pub. Date: May 26, 2016

(65) Prior Publication Data
US 2017/0333130 A1    Nov. 23, 2017

(30) Foreign Application Priority Data

Nov. 18, 2014  (SE) ..................... 1451384

(51) Int. Cl.
*A61B 18/24*     (2006.01)
*A61M 25/00*     (2006.01)
(Continued)

(52) U.S. Cl.
CPC ......... *A61B 18/24* (2013.01); *A61M 25/0084* (2013.01); *A61M 25/01* (2013.01);
(Continued)

(58) Field of Classification Search
CPC ............ A61M 25/007; A61M 25/0082; A61M 25/0084; A61M 2025/0188;
(Continued)

(56) References Cited

U.S. PATENT DOCUMENTS 4,832,024 A    5/1989  Boussignac et al.
8,308,709 B2   11/2012 Chang
(Continued)

FOREIGN PATENT DOCUMENTS

CN    1204242 A    1/1999
EP    0876804 A1   11/1998
(Continued)

*Primary Examiner* — Laura A Bouchelle
*Assistant Examiner* — Anh Bui
(74) *Attorney, Agent, or Firm* — Capitol City TechLaw

(57) ABSTRACT

A medical device to be inserted in a defect blood vessel, body cavity, or body duct for treatment thereof is disclosed, wherein it comprises an essentially cylindrically formed elongated resilient sheath device (2) wherein it has a distal end (3) and a proximal end (4), wherein said sheath device (2) along its circumferential surface in the axial direction is provided with a slotted opening (5) having connection with a first bore (6) arranged in the axial direction of said sheath device (2), said first bore (6) having the ability to house an elongated fiber body (7), wherein said sheath device (2) has the ability to be clamped around a major part of the perimeter of said fiber body (7), and wherein said sheath device (2) in its axial direction also is provided with a second bore (8) having the ability to house an injection means (9), as well as a kit containing said medical device, and a method for treatment of defective blood vessels, body cavities, and body ducts by use of said medical device.

22 Claims, 2 Drawing Sheets

(51) Int. Cl.
*A61M 25/01* (2006.01)
*A61B 18/00* (2006.01)

(52) U.S. Cl.
CPC .............. *A61B 2018/00345* (2013.01); *A61B 2018/00404* (2013.01); *A61B 2018/00577* (2013.01); *A61M 25/008* (2013.01); *A61M 2025/0034* (2013.01); *A61M 2025/0089* (2013.01); *A61M 2025/0188* (2013.01)

(58) Field of Classification Search
CPC ........... A61M 2025/0034; A61B 18/24; A61B 2018/00345
See application file for complete search history.

(56) References Cited

U.S. PATENT DOCUMENTS

| | | |
|---|---|---|
| 8,454,586 B2 | 6/2013 | Anastasie |
| 8,465,451 B2 | 6/2013 | McRae et al. |
| 2003/0032936 A1 | 2/2003 | Lederman |
| 2004/0254528 A1* | 12/2004 | Adams .................. A61M 25/00 604/96.01 |
| 2005/0278010 A1 | 12/2005 | Richardson |
| 2006/0293647 A1* | 12/2006 | McRae ............... A61B 18/1492 606/27 |
| 2008/0009770 A1* | 1/2008 | Weber ....................... A61F 2/95 600/585 |
| 2008/0015409 A1 | 1/2008 | Barlow et al. |
| 2009/0131924 A1 | 5/2009 | Meyer et al. |
| 2009/0222003 A1 | 9/2009 | Otley |
| 2011/0031980 A1 | 2/2011 | Kruger et al. |
| 2014/0100460 A1 | 4/2014 | Otley |
| 2014/0135661 A1 | 5/2014 | Garrison et al. |

FOREIGN PATENT DOCUMENTS

| | | |
|---|---|---|
| EP | 1350481 A2 | 10/2003 |
| EP | 1853204 A1 | 11/2007 |
| RU | 2506921 C2 | 2/2014 |
| WO | 2006/093550 A1 | 9/2006 |
| WO | 2007058877 A2 | 5/2007 |
| WO | 2007102586 A1 | 9/2007 |
| WO | 2015061614 A1 | 4/2015 |

* cited by examiner

MEDICAL DEVICE FOR TREATMENT OF DEFECTIVE BLOOD VESSELS, BODY CAVITIES, AND BODY DUCTS

This application claims priority under 35 USC 119(a)-(d) to SE 1451384-0, which was filed on Nov. 18, 2014, the entire content of which is incorporated herein by reference.

TECHNICAL FIELD OF THE INVENTION

The present invention relates to a device for treatment of defective blood vessels, body cavities, and body ducts, to a kit for said treatment, to use of the device and the kit for said treatment, and to a method for treatment of defective blood vessels, body cavities, and body ducts.

BACKGROUND ART

Varicose veins are veins that have become enlarged and tortuous. The term commonly refers to the veins on the legs, although varicose veins can occur elsewhere in the inferior part of the body. Veins are provided with leaflet valves to prevent retrograde flow or reflux of blood, i.e. a backwards flow of blood. Leg muscles pump the veins to return blood to the heart (the skeletal-muscle pump) against the effects of gravity. When veins become varicose, the leaflets of the valves no longer meet properly, and the valves do not work, i.e. a valvular incompetence occurs. This allows blood to flow backwards and the veins enlarge even more. Varicose veins occurs in the superficial veins of the legs, e.g. in the saphenous veins, which are subject to high pressure when standing. Besides being a cosmetic problem, varicose veins can be painful, especially when standing. Severe long-standing varicose veins can lead to leg swelling, venous eczema, skin thickening (lipodermatosclerosis), and ulceration. Life-threatening complications are uncommon, but varicose veins may be confused with deep vein thrombosis, which can be a life-threatening condition.

Non-surgical treatments of varicose veins include elastic stockings, elevation of the legs, exercise, and sclerotherapy. The traditional surgical treatment has been vein stripping with a view to removing the affected veins. Newer, less invasive treatments which seal the main leaking vein are available, such as ultrasound-guided foam sclerotherapy, radio frequency ablation and endovenous laser treatment. Because most of the blood in the legs is returned by the deep veins, the superficial veins, which returns only less than 10% of the total blood of the legs, can usually be removed or ablated without any harm.

Secondary varicose veins are those developing as collateral pathways, typically after stenosis or occlusion of the deep veins, a common complication of extensive deep venous thrombosis (DVT). Treatment options are usually support stockings, occasionally sclerotherapy, and rarely limited surgery.

As mentioned above, at present varicose veins may be treated by endovenous laser (EVL) or radiofrequency (RF) ablation by using a fiber acting when inserted in the vein to be treated. The fiber is inserted into the vein via a puncture hole on the skin of the patient using the Seldinger technique. This technique involves the insertion of a sharp hollow needle, also called a trocar, through the skin into the blood vessel or cavity in question, e.g. a vein. If necessary, ultrasound guidance can be used. Then a guidewire is advanced through the lumen of the needle, and thereafter the needle is withdrawn. Thereafter, an introducer sheath or a blunt cannula is passed over the guidewire into the vessel or cavity. Then the guidewire is withdrawn through the lumen of the introducer sheath. The introducer sheath can be used to introduce catheters or other devices with a view to performing endoluminal procedures, i.e. inside the hollow body part which has been punctured. Interventional procedures, such as the above-mentioned EVL and RF ablation, are often used for treatment of varicose veins. In such a case a short, approximately 10 cm long introducer sheath is provided in the vein by use of said Seldinger technique. During the treatment of varicose veins a fiber body is introduced into the vein via the introducer sheath having its inlet port close to the puncture hole on the skin of the patient. Said fiber body is then introduced with a certain length until the location of the treatment start has been reached. In the case of treatment of varicose veins, the fiber body may be introduced as long as up to 90 cm from the puncture hole in the skin of the patient. Normally, the fiber body is introduced approximately 40 cm.

The heat producing parts of the fiber is located in the distal end of the fiber body, i.e. in the end most far away from the puncture hole on the skin when the fiber body has been inserted in its full length. During treatment the fiber part in the distal end of the fiber body emits laser or heat energy to the surrounding wall of the vein. Then the structure of the vein wall is burned and destroyed, and the vein will close or occlude. As initially suggested, the treatment of varicose veins is normally performed in the saphenous veins, which often not are visible from the exterior. Instead, it is the connecting smaller superficial veins that give rise to the cosmetic problems experienced. By destroying the saphenous veins with heat, the superficial veins will lose their high pressure back flow and blood supply and will therefore shrink to normal size. By time, the veins will regress and gradually be less visible on the patient's skin surface. The blood run-off of the treated leg will still be enough for the normal function of the leg, although one or more saphenous veins have been destroyed.

The treatment of varicose veins with EVL or RF ablation is performed by gentle incremental withdrawal of the fiber body out from the treated vein until the whole insufficient part of the vein has been treated. During EVL or RF treatment along the interior wall of the vein, the fiber body emits laser radiation or heat to the vein wall and exerts its intentional destroying action. Such a treatment is substantially painful and requires a preceding anesthetization. This has so far been performed by general anesthetization or local external injection of an anesthetic with a syringe on the external skin at several positions in parallel along the vein to be treated, as close as possible to the vein. This repeated injection procedure may involve more than 30 injections, wherein each one is painful and uncomfortable for the patients due to the rich presence of pain receptors in the skin. This is a substantial problem which can be solved by anesthetization from the inside of the vein.

EP 1 350 481 discloses a medical device for treatment of e.g. varicose veins, wherein an optical laser fiber inserted in the vein to be treated is enclosed by a catheter. Anesthetic fluid is brought to advance into the annular fluid passageway formed between the optical fiber and the inner side wall of the catheter. A plurality of exits is disposed along the length of a segment of the catheter corresponding to a portion of the vein to be treated. Said plurality of exits is pressure-responsive and is arranged to be opened in response to an internal fluid pressure. In such a way, anesthetic fluid may be administered to the inner wall of the vein in its longitudinal direction, thereby avoiding the problem with repeated external painful injections of anesthetic fluid.

U.S. Pat. No. 8,465,451 discloses a catheter for treatment of a hollow anatomical structure, e.g. a vein. Said catheter further comprises at least one radially expandable transmural fluid delivery channel, as well as a shaft provided with radially extendable needles having the ability to pass through needle holes in the catheter wall and inject tumescent fluid into the vein inner wall.

U.S. Pat. No. 8,308,709 also discloses devices for selectively injecting fluids to a target tissue from within a blood vessel. US 2014/0135661, US 2011/031980, and U.S. Pat. No. 8,454,586 also disclose methods and devices for selectively applying fluids to a target tissue from within a blood vessel.

Although methods of injecting anesthetic fluids from within a blood vessel are known, none of them are at present used in practice for ablation treatment of blood vessels, such as for treatment of varicose veins, as they have too large diameters for the blood vessel, are technically rather complicated, and are difficult to handle, leading to the consequence that the anesthetizing agent does not reach its target tissue in a satisfactory way enough.

A common problem with the known devices for applying medical fluids to a target tissue from within a blood vessel is that the components of the device requires a substantial volume within the blood vessel to be treated. More precisely, the cross-section area of the lumen of the blood vessel to be treated is almost fully occupied with said components, thereby inducing a risk for damage of the vein wall during the introduction of the devices and also causing undesired spasms of the vein wall, which would prevent further treatment possibilities. A further common problem with known devices is that a lot of treatment steps are required in connection with treatment of e.g. varicose veins. Another problem in the known art is that a repeated anesthetization is difficult to perform in the case the anesthetization effect of the vein wall and surrounding tissue would cease. Thus, there is a need of an improved medical device and an improved method in connection with ablation treatment of blood vessels, in particular varicose veins, but also of other defective body cavities or ducts, wherein the above-mentioned problems are avoided.

SUMMARY OF THE INVENTION

An object of the present invention is to provide an improved medical device and an improved method for treatment, preferably ablation treatment, of defective blood vessels, body cavities, and body ducts by which the above-mentioned problems are solved.

This object is achieved with a medical device according to claim 1. The object is also obtained with a kit comprising said medical device and with a treatment method involving the use of said medical device. Particular and preferred embodiments are disclosed in the subsequent dependent claims.

In one aspect the present invention refers to a medical device to be inserted in a defect blood vessel, body cavity, or body duct for treatment, preferably ablation treatment, comprising an essentially cylindrically formed elongated resilient sheath device 2 wherein it has a distal end 3 and a proximal end 4, wherein said sheath device 2 along its circumferential surface in the axial direction is provided with a slotted opening 5 having connection with a first bore 6 arranged in the axial direction of said sheath device 2, said first bore 6 having the ability to house an elongated fiber body 7, wherein said sheath device 2 has the ability to be clamped around a major part of the perimeter of said fiber body 7, and wherein said sheath device 2 in its axial direction also is provided with a second bore 8 having the ability to house an injection means 9.

In another aspect the present invention refers to a kit for treatment, preferably ablation treatment, of defective blood vessels, body cavities, and body ducts, wherein said kit comprises said medical device, the fiber body 7, and the injection means 9.

In still another aspect the present invention refers to use of the medical device according to claim 1 for the treatment, preferably ablation treatment, of defective blood vessels, body cavities, and body ducts.

In a further aspect the present invention refers to a method for treatment, preferably ablation treatment, of defective blood vessels, body cavities, and body ducts, preferably varicose veins, or for the deposition of a medical fluid in the tissue surrounding defective blood vessels, body cavities, and body ducts, wherein it in the case of ablation treatment comprises the steps of:

a) insertion of the medical device according to claim 1, the fiber body (7), and the injection means (9) in the lumen (14) of a blood vessel, body cavity, or body duct until a predetermined location is reached, wherein the fiber body (7) is inserted via the first bore (6) and the injection means is inserted via the second bore (8), b) pressing the injection means (9) out from the second bore (8), wherein the needle tip of said injection means (9) deviates in a radial direction, passes through the wall of the blood vessel, body cavity, or body duct, and reaches the perivascular tissue (13) or the surrounding tissue, c) injection of a medical fluid into the perivascular tissue (13) or the surrounding tissue, d) withdrawing the injection means (9) back into the second bore (8), e) withdrawing the sheath device (2) and the injection means (9) in a proximal direction until a new predetermined injection site has been reached, wherein the fiber body (7) not is withdrawn, f) repeating steps b)-e) until the walls of the blood vessel, body cavity, or body duct and the perivascular tissue (13) or the surrounding tissue along the whole part of the blood vessel, body cavity, or body duct has been anesthetized, g) eliminating the sheath device (2) and the injection means (9) from the lumen (14) of the blood vessel, body cavity, or body duct, h) performing the treatment of the inner walls of the blood vessel, body cavity, or body duct by use of the fiber body (7), wherein said fiber body (7) is incrementally withdrawn in the proximal direction in the lumen (14) until the whole part of the inner wall surface of the blood vessel, body cavity, or body duct to be treated has been subjected to the treatment, and i) withdrawing the fiber body (7) from the lumen (14) of the blood vessel, body cavity, or body duct, wherein said medical fluid has a tumescent and/or anesthetizing activity, and wherein it in the case of the deposition of a medical fluid in said tissue comprises use of the medical device according to claim 1 or the kit according to claim 10, optionally without the fiber body (7), in at least the method steps a)-f) above, wherein said medical fluid preferably is a fluid having tumescent and/or anesthetizing activity, cytostatic activity, or sclerosant activity.

DETAILED DESCRIPTION OF THE INVENTION AND PREFERRED EMBODIMENTS THEREOF

Figure 1:
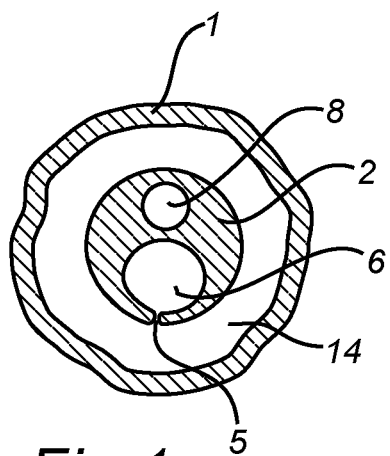
FIG. 1 is a cross-sectional view of a vein 1 in which the medical device according to the present invention for the ablation treatment of varicose veins, shown from the distal end surface of the sheath device 2, is inserted.

First, some expressions present in the application text will be defined.

The expression "defective" used throughout the application text in connection with blood vessel, body cavity and body duct is intended to mean that the blood vessel, body cavity and body duct is subject to a condition which can be regarded to be abnormal, dysfunctional or pathological. This also includes the situation when the presence of the body cavity as such is abnormal, e.g. when the body cavity constitutes a tumor or a cyst.

The expression "ablation" used throughout the application text is intended to mean the process where an anatomic surface is eliminated or destroyed.

The expression "essentially cylindrically formed" used throughout the application text is intended to mean that deviations from a cylindrical form of the object in question also may be effective when carrying out the present invention, as long as the geometry of the object fits well in the blood vessel, body cavity, body duct, or bore in which it is to be located. The same principle applies for the terms "essentially circular", "essentially oval" and "essentially axial", also used throughout the application text.

The expression "distal end" used throughout the application text is intended to mean the end of the element in question of the medical device or the kit according to the present invention which is to be inserted first in the blood vessel, body cavity, body duct, or bore in question during the ablation treatment.

The expression "proximal end" used throughout the application text is intended to mean the opposite end of the "distal end" defined above.

It should be noted that the expressions "distal end" and "proximal end" do not have their conventional meanings, which otherwise are the opposite, in connection with conventional blood vessel direction terminology.

The expression "perivascular tissue" used throughout the application text is intended to mean the tissue part surrounding the blood vessel to be treated. This tissue part may contain fat, muscles, and/or connective tissue, and is normally a non-clearly delimited tissue volume within the body.

The expression "surrounding tissue" used throughout the application text is intended to mean the tissue part surrounding the body cavity or body duct to be treated. The surrounding tissue may vary to great extent depending on the nature of the body cavity or duct, but may also contain fat, muscles, and/or connective tissue.

The expression "tumescent fluid" used throughout the application text may be characterized to be a fluid having the ability to create intentional swelling, or tumescense, of a body tissue. In some cases a tumescent fluid may be an anesthetic fluid at the same time having both a tumescent and an anesthetization action, which is the case for the present invention.

The veins to be treated in the case of varicose veins normally have an inner diameter of about 10 mm, after which the dimensions of the medical device according to the present invention is adapted. In the case of larger body cavities to treat, the dimensions of the medical device are increased correspondingly.

The advantages achievable with the present invention are that the deployment of tumescent around the vein to be treated will become simpler because of the short distance to the perivascular tissue, in the case of blood vessels, and the surrounding tissue, in the case of a body cavity or duct, which will increase the accuracy of the deployment of the tumescent. This will not only have the effect of less peroperative and postoperative pain for the patient but also better treatment effect, due to that compression of the vein closer to the fiber body will be better, which will enhance the effect of the treatment. Moreover, the tumescent forms an isolating liquid layer around the vein to be treated. This layer protects the surrounding tissues from the heat, which will diminish the postoperative pain. The fiber body also acts as a stabilizing support during the anesthetization step, which will minimize and simplify the use of the device compared to other similar devices. A further advantage is that the device may be used repeatedly in a simpler way, e.g. if further anesthetization would be needed, which is disclosed more in detail below.

The present invention will now be disclosed more in detail with reference to the Drawings, in which the medical device and the kit according to the present invention are represented by the embodiment intended for ablation treatment of varicose veins.

Referring to FIG. 1, which is a cross-sectional view from the distal end surface of a sheath device 2, said sheath device 2 has an overall essentially circular cross-section, except from the part containing a slotted opening 5. Deviations of a perfectly circular cross-section may also be effective, provided that they are in conformity with the lumen 14 of a vein 1, which is shown in FIG. 1 as an example of the defective blood vessel. The outer cross-section diameter of the sheath device 2 is of course necessary smaller than the inner diameter of the lumen 14 of the vein 1. The outer cross-section diameter of the sheath device 2 is at least 4 F (1.27 mm) and may be up to 34 F (10.82 mm) in the case of treatment of aorta and bronchi. In one embodiment, e.g. when the saphenous vein is to be treated, the outer cross-section diameter of the sheath device 2 is 4-8 F (French) (1.27-2.56 mm), preferably 5-7 F (1.59-2.23), most preferably 6 F (1.91 mm), wherein 1 F corresponds to $1/\pi$ mm. The exact diameter varies with the inner diameter of the lumen 14 of the vein 1, in particular in the case when the walls of the vein 1 are irregularly formed and/or when the vein 1 to be treated has an overall winding structure. The clearance in the lumen 14 between the inner wall of the vein 1 and the circumferential surface of the sheath device 2 may vary depending on the inner surface structure of the vein 1, which may irregular.

In one embodiment the sheath device 2 is an integral body. In another embodiment the sheath device 2 is composite body assembled by several different parts. Said sheath device 2 is manufactured of a body compatible material commonly used for intervention catheters in the medical area. Such a material is normally manufactured of a polymer material or a polymer blend material. In one embodiment of the sheath device 2 the distal end 3 thereof may alternatively be manufactured of a body compatible metal material, such as up to some centimeters, e.g. up to 3 centimeters, of the outermost part of the distal end 3 with a view to strengthening the durability of the sheath device 2. Said distal end 3 of the sheath device 2 may be manufactured of a metal material either integrally or only in the region of the exterior surfaces thereof down to a certain depth, while the inner parts in the latter case are manufactured by a polymer material.

In one embodiment the surface of the distal end 3 of the sheath device 2 is blunt, as shown in FIG. 1, but deviations thereof may exist. In FIG. 1 the port of a first bore 6 running axially through the whole of the sheath device 2 is shown, as well as the slotted opening 5, also running axially through the whole of the sheath device 2. Said first bore 6 has the capability of housing a fiber body 7 (not shown in FIG. 1 but in FIG. 2). The cross-section of the first bore 6 is circular or essentially circular, except from the minor part that is connected to the slotted opening 5. Deviations of a perfectly circular cross-section may also be effective, provided that they are in conformity with the fiber body 7 to be housed therein. The first bore 6 has in one embodiment a diameter of 3-5 F (0.96-1.59 mm), preferably 3.5-4.5 F (1.11-1.43 mm) in case of treatment of varicose veins, but may also be more than so for a sheath device intended for treatment of e.g. aorta and bronchi. As stated above, the first bore 6 runs in one embodiment in the axial direction of the sheath device 2, but may also slightly deviate, as long as its capability of housing the fiber body 7 not is negatively influenced, i.e. makes it difficult for the fiber body 7 to slide within the first bore 6.

The outer diameter of the fiber body 7 should be adapted to the diameter of the first bore 6 in such a way that the fiber body 7 is slidably arranged within the first bore 6, e.g. when the sheath device 2 is withdrawn from the vein 1 during the treatment procedure, wherein the fiber body 7 is maintained in its initial location. The inner surface of the first bore 6 and/or the circumferential surface of the fiber body 7 may have been subjected to a preceding surface treatment with a view to increasing the sliding ability between the two surfaces in question. E.g., these polymeric surface(s) may have been treated with silicone or have been provided with a hydrophilic coating. After having been clamped within the first bore 6 by first opening and then closing the slotted opening 5 of the resilient sheath device 2, the fiber body 7 is held tightly in place within the sheath device 2, allowing only sliding movement in axial direction within the first bore 6.

This means that the slotted opening 5 has to be small enough for the fiber body 7 not to run the risk of being pressed out from the first bore 6 via the slotted opening 5 to the lumen 14 during the treatment procedure. The slotted opening 5 of the sheath device 2 is represented by a gap between the two edges facing each other along the sheath device 2, thereby giving the sheath device 2 an essentially U-formed cross-section. The width of said gap is not critical as long as the sheath device 2 has the ability to clamp a major part of the perimeter of the fiber body 7 and safely secure the fiber body 7 when clamped in place within the first bore 6, i.e. such that the fiber body 7 not may slip out from the first bore 6. In such an embodiment the gap can be up to 1.3 millimeters. In the case the fiber body 7 not yet has been introduced in the first bore 6 of the sheath device 2, the gap width may be negligible, i.e. may be up to at most 0.1 millimeter, wherein said edges of the sheath device 2 are in a slight contact with each other. Per definition, the sheath device 2 and the first bore 6 thereof must have the ability to clamp and safely secure a fiber device 7 having a cross-sectional diameter of at most 6 FR (1.91 mm).

One substantial advantage with the slotted opening 5 along the sheath device 2 is that the said sheath device 2 in its axial direction and the injection needle 9 contained in the second bore 8 may easily be clamped around the fiber body 7 in the case it would turn out to be necessary with a repeated anesthetization after that a previous anesthetization step already has been performed and the sheath device 2 and the injection needle have been withdrawn from the patient. Thus, this clamping step may be performed extracorporeally. The fiber body 7 is also extracorporeally connected to a generator (shown in FIG. 4) of laser or radiofrequency energy in such a way that the fiber body 7, the generator, and the means required for connecting the generator and the fiber body 7 are integrally arranged with a view to securing a proper delivery of the laser light without any risk for malfunction of the laser light. If the sheath device 2 would have been provided with a closed first bore 6, i.e. would lack the slotted opening 5, the whole fiber body 7 would have to be taken out from e.g. the blood vessel in the case of the need of a repeated anesthetization and to be inserted again for further treatment, which would involve additional mechanical interventions by the operator, thereby jeopardizing a proper re-positioning of the laser body 7 and the accuracy of the whole ablation process. Thus, with the fiber and laser generator equipment used in practice today, this is an unavoidable drawback. This drawback is eliminated with the presence of the slotted opening 5 of the sheath device 2.

Another substantial advantage with the slotted opening 5 is that the total cross-section area of the structure to be inserted in a blood vessel or in another body cavity or duct to treat, i.e. the sheath device 2, the fiber body 7, and the injection means 9, becomes smaller compared to conventionally used structures. Thereby, the risk of undesired spasms and lesions in the inner walls of the blood vessel, body cavity or body duct during the insertion step is reduced.

The sheath device 2 is also provided with a second bore 8 running in parallel or essentially in parallel with the bore 6. Said second bore 8 has the capability of housing an injection means 9. The diameter of the second bore 8 depends on the outer diameter of the injection means 9 to be located therein, which normally is 20-22 gauge (0.90-0.71 mm). Thus, the diameter of the bore is slightly larger than the outer diameter of the injection means 9, i.e. some parts of a millimeter larger. Both the first bore 6 and the second bore 8 ends in the distal end 3 of the sheath device 2 and runs both to the proximal end of the sheath device 2. The shortest distance between the first bore 6 and the second bore 8 within the sheath device 2 depends on the material of which the medical device is manufactured and should not be such small that the section between these along the sheath device 2 becomes fragile when housing the fiber body 7 and the injection means 9, respectively. Normally, said shortest distance is from some parts of a millimeter, and up to 0.5 mm. The location of the second bore 8 in relation to the slotted opening 5 is not critical, but in one embodiment the first bore 6 is located between the slotted opening 5 and the second bore 8, as is shown in FIG. 1.

Figure 2:
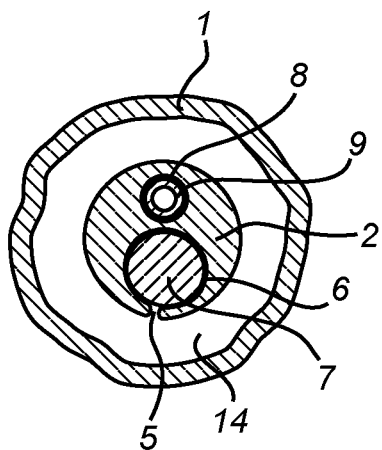
FIG. 2 is the same cross-sectional view as in FIG. 1, wherein in addition a fiber body 7, shown from its distal end surface, and an injection means 9, shown from its distal end surface, is located within the first bore 6 and the second bore 8, respectively, of the sheath device 2.

FIG. 2 is also a cross-sectional view from the distal end surface of the sheath device 2, but also schematically shows the situation when a fiber body 7 and an injection means 9 is located in the first bore 6 and the second bore 8, respectively. The fiber body 7 may be any conventional fiber body used in the medical area, e.g. for treatment of varicose veins.

All kinds of fiber bodies 7 among the conventional laser fibers and radiofrequency fibers present on the market can be used in connection with the present invention, provided that they have the correct dimensions. The fiber body 7 is in its distal end provided with means for the laser or radiofrequency induced ablation of the inner wall surface of the blood vessel, body cavity or body duct to be treated. According to the present invention the fiber body 7, or at least parts thereof, should be resilient with a view to facilitating the insertion thereof in the blood vessel to be treated as well as the withdrawal thereof. The fiber body 7 should at the same time be enough rigid to be able to act as guide support when the sheath device 2 is introduced in the blood vessel, body cavity or body duct to be treated.

FIG. 2 also shows the injection means 9 located in the second bore 8 of the sheath device 2. The outer diameter of the injection means 9 should be adapted to the diameter of the second bore 8 in such a way that the injection means 9 easily can be axially moved through the second bore 8 leaving a small clearance therein. The inner surface of the second bore 8 and the circumferential surface of the injection means 9 may have been subjected to a preceding surface treatment with a view to increasing the sliding action of the injection means 9 in the second bore 8. E.g., the inner surface of the second bore 8 may have been treated with silicone or have been provided with a hydrophilic coating. As the outermost part of the distal end 3 of the sheath device 2, e.g. up to 3 centimeters thereof, may be manufactured of a metal material, as discussed above, the inner surface of said outermost part of the distal end 3 of the second bore 8 automatically is manufactured of a metal material. In another embodiment of the invention, the inner surface of the outermost part of the distal end 3 of the second bore 8, e.g. up to 3 cm thereof, may be provided with or manufactured of a metal in a layer down to a certain depth of said inner surface, while the remaining part of the sheath device 2 is not at all manufactured of a metal, or while the sheath device 2 at its exterior surfaces in the outermost part of the distal end 3, e.g. up to 3 cm thereof, fully or partially also is provided with or manufactured by a metal in a layer down to a certain depth. Thereby, the inner surface of the second bore 8 is protected from damage in the case the injection means 9 would accidentally hit said inner surface. The injections means 9 can be any conventional injection device used in the medical area, e.g. any kind of injection needle. The injection means 9 is in one embodiment axially located in the second bore 8, which may have a circular or essentially circular cross-section, or an oval or essentially oval cross-section. Geometrical deviations thereof, such as a slightly non-axial location and a slightly non-circular cross-section may also be effective as long as the sliding or moving action of the injection means 9 within the second bore 8 is not negatively affected. In one embodiment the cross-section area of the injection means 9 is in conformance with the cross-sectional area of the second bore 8 and may e.g. also be oval.

According to the present invention the needle tip of the injection means 9 has to be able to deviate in the radial direction when pressed out from the port of the second bore 8 in the distal end surface of the sheath device 2. The needle tip follows a curved line in the lumen 14 until it reaches the inner surface of the blood vessel, body cavity or body duct to anesthetize, e.g. a vein 1. This may in one embodiment be accomplished by using an injection means 9 manufactured of a material prepared to show such a behavior, such as a metal material having a memory effect. Such metal materials are conventional, and one useful example is a Nitinol alloy.

Thus, when still located within the second bore 8 the injection means 9 only extends in an axial or essentially axial direction, but when the injection device 9 is pressed out from the second bore 8, the needle tip of the injection means 9 immediately starts to deviate following a curved line in the lumen 14 until it reaches the anesthetization site of the above-mentioned inner surface. The distance between the needle tip in the moment it protrudes from the second bore 8 and the inner surface of a vein is normally approximately 3-4 mm.

Figure 3:
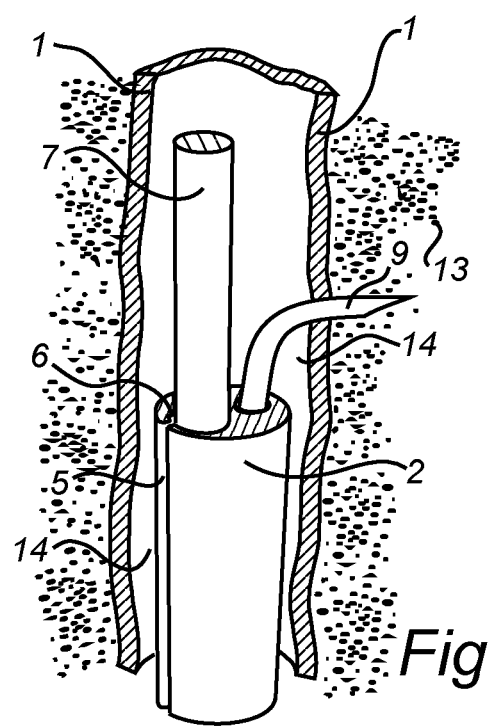
FIG. 3 is a perspective view of a distal part of the kit according to the present invention in action during the initial anesthetization step in the method for ablation treatment of varicose veins.

As appears from FIG. 3, the needle tip of the injection means 9 is normally also facet cut in its ultimate distal end in such a way that the pointed part of the needle tip does not come in contact with the inner surface of the second bore 8 in any harmful way before the injection needle 9 is pressed out from said second bore 8. The direction of the injection means 9, as well as the degree of anesthetization of the perivascular tissue 13, may be followed visually via ultrasound.

The injection means 9 is also arranged in such a way that the needle tip during the injection step each time is directed against the surrounding inner wall of the blood vessel, body cavity or body duct to anesthetize when the injection means 9 is pressed out from the second bore 8. That is, the needle tip each time deviates outwardly in the radial direction. This is achieved by securing the injection means 9 to the sheath device 2 somewhere along the second bore 8 and/or extracorporeally in the regulation means 11, and/or somewhere between, in such a way that said outwardly radial direction always is obtained. Thereby, the situation when the needle tip of the injection device 9 would come in contact with the fiber body 7 during the anesthetization step is avoided. With a view to obtaining an even and homogenous anesthetization along the whole blood vessel, body cavity or body duct to treat, it is often enough to anesthetize along a vertical line within a blood vessel. The anesthetization and tumescence degree may be followed visually via ultrasound. However, in some cases such an injection mode is not enough for obtaining a proper anesthetization and tumescence, and if so, the injection site may be varied in the horizontal plane between each injection step by extracorporeally induced rotation of the sheath device 2 including the fiber body 7 and the injection means 9. The sheath device 2 may be rotated manually by the operator. In such a way, an evenly distributed anesthetization throughout the whole blood vessel, body cavity or body duct is obtained. The whole system containing the fiber body 7, the sheath device 2, and the injection means 9 may be rotated together.

As disclosed above, the needle tip of the injection means 9 is pressed out from the second bore 8 during the injection step until it reaches the inner wall surface of the blood vessel, body cavity or body duct to anesthetize. In the case of a vein it is further pressed transmurally until it has passed said vein wall, which has a thickness of some tenths of a millimeter, and is finally pressed into the perivascular tissue 13. At a distance of approximately 2-3 mm into the perivascular tissue 13 the medical fluid, e.g. tumescent and/or anesthetic fluid, is injected. In the case of a defect body cavity or duct to anesthetize, the injection is made in the corresponding tissue surrounding said body cavity or duct. Thereafter, the injection means 9 is withdrawn all the way back into the second bore 8. Then the sheath device 2 including the injection means 9 is withdrawn in a proximal direction until the next predetermined injection site is reached. The sheath device 2 including the injection means 9 and the fiber body 7 is then, if necessary, rotated in the horizontal plane in such a way that the next injection site in the blood vessel, body cavity or body duct to anesthetize is not located in line in the axial direction in relation to the most previous injection site(s). Thus, in the case of a vein, the injection sites could be located in a spiral formed arrangement on the inner wall of the vein. Further, in the case of anesthetization of veins, the sheath device 2 including the injection means 9 is withdrawn in the proximal direction with approximately 10-70 mm and can be rotated in an angle of 90-180° at a time between each anesthetization step. Moreover, approximately 8-15 injections are normally needed for an adequate anesthetization of a vein.

The arrangement of the injection means 9 in the medical device according to the present invention may be adapted to the blood vessel, body cavity or body duct in question to anesthetize. If e.g. the surrounding tissues of a larger body cavity are to be anesthetized, the injection means 9 may be adapted to protrude from the second bore 8 a longer distance in the radial direction compared to the vein anesthetization embodiment until the desired end position for the injection in the surrounding tissue has been reached.

FIG. 3 shows in a perspective view the sheath device 2 during use in the treatment of varicose veins within the lumen 14 of a vein 1. In FIG. 3 the fiber body 7 having its active laser or radiofrequency emitting part in its distal end protrudes from the first bore 6 of the sheath device 2, which has been withdrawn a certain distance in the proximal direction. The injection means 9 protrudes from the second bore 8 of the sheath device 2, wherein the needle tip thereof has been deviated in the radial direction and been pressed forward in such a way that the needle tip has passed through the wall of the vein 1 and into the perivascular tissue 13. In FIG. 3 a situation is shown when several injections of the vein 1 already has been performed, as, inter alia, appears from the location of the fiber body 7 in relation to the distal end of the sheath device 2 and the injection means 9.

Figure 4:
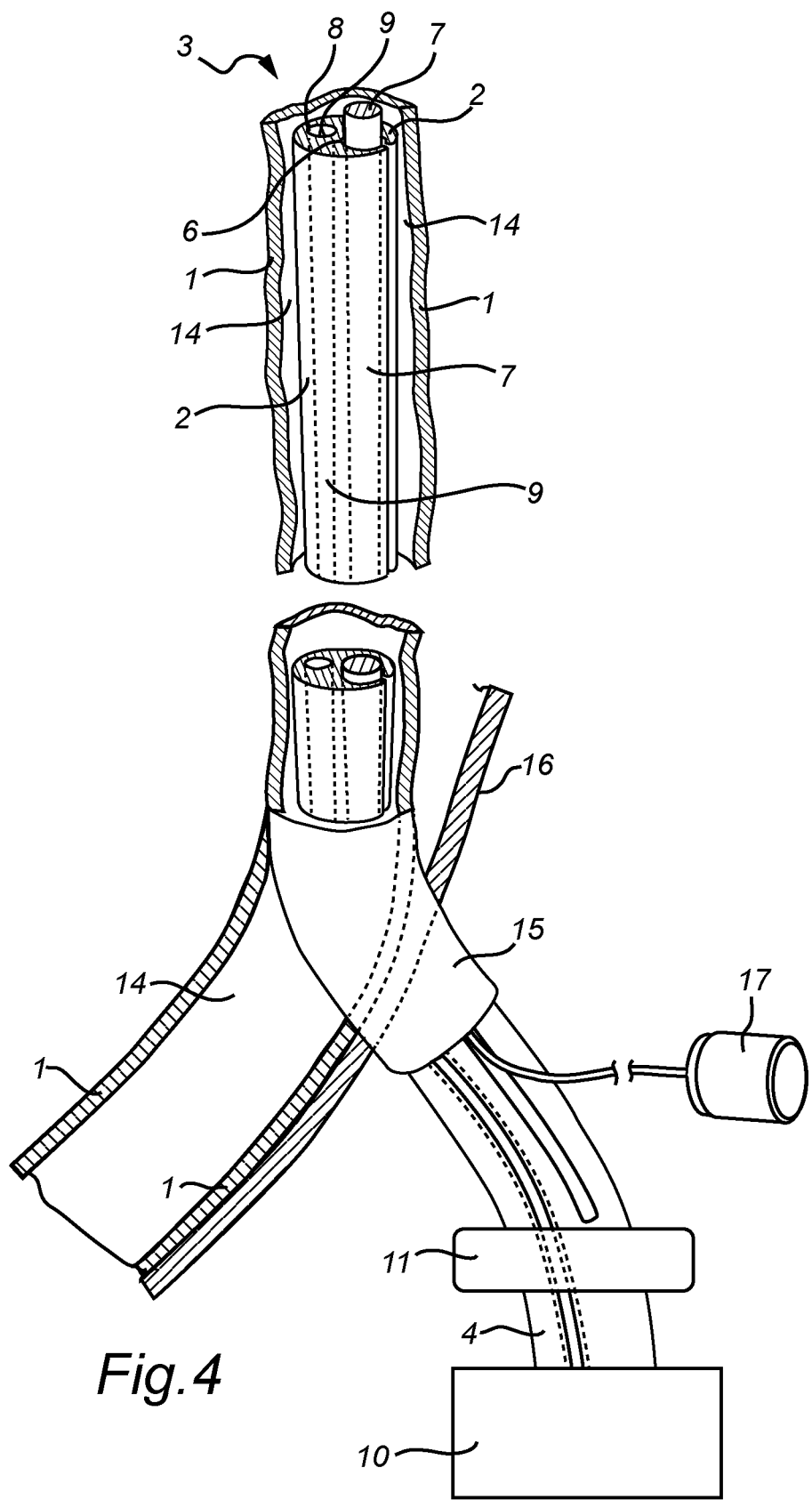
FIG. 4 is a perspective view of the whole kit according to the present invention.

FIG. 4 shows the kit according to the present invention connected to a vein 1. Said kit comprises the medical device according to the present invention, in which the fiber body 7 is located within the first bore 6 of the sheath device 2 and the injection means 9 is located in the second bore 8 of the sheath device 2. Said kit also comprises a container for medical fluid 10 and a regulation means 11, and these are extracorporeally located in the proximal end 4 of the sheath device 2 close to an introducer sheath 15 constituting the inlet port in the skin 16 to the vein 1. The introducer sheath 15 is actually a remaining part of the longer introducer sheath initially used for obtaining access to the vein 1, such as in the Seldinger technique discussed above. Said introducer sheath 15 may also be provided with a check valve (not shown in FIG. 4) in its distal end, which in turn may be connected to a three-way-valve via a conduit (not shown in FIG. 4) with a view to provide for any addition of e.g. rinse solutions, drug solutions, etc. The injection means 9 is in its proximal end fluidly connected with the container for medical fluid 10. The flow of the medical fluid into the vein for the anesthetization treatment is regulated by a regulation means 11 connected between the container for medical fluid 10 and the introducer sheath 15. Said regulation means 11 may be any conventional fluid flow regulator or dosage device providing a predetermined fluid volume, but is in one embodiment a pistol with a trigger. A pump (not shown in FIG. 4) for forcing the medical fluid is also connected to the container for the medical fluid 10 and the regulation means 11.

The proximal end of the fiber body 7 protrudes extracorporeally from the slotted opening 5 of the sheath device 2 and is directly connected to a generator 17 of the laser or the radiofrequency ablation treatment.

After the above-disclosed anesthetization step has been performed and the sheath device 2 containing the injection means 9 has been totally withdrawn from the anesthetized blood vessel, the body cavity or the body duct, the laser or radiofrequency ablation treatment is initiated.

During the laser or radiofrequency ablation treatment the fiber body 7 is first withdrawn a short distance, e.g. approximately 10 mm, from its initial position in the proximal direction. Thereby, the risk is reduced for ablation of a part of the blood vessel, the body cavity or the body duct to be treated which has not been adequately anesthetized during the initial anesthetization step in the distal end of the sheath device 2. The generator 17 is switched on, and then the fiber body 7 is manually or automatically withdrawn in a proximal direction with a certain speed. In one embodiment the withdrawal speed is approximately 70 J/cm. The withdrawal action is manually performed, and the on and off setting of the laser generator 17 may be controlled with a foot pedal. Further, a centimeter scale provided on the fiber body 7 may facilitate the correct withdrawal speed. The ablation process may also be followed via ultrasound. After the ablation step the fiber body is totally withdrawn from the ablated blood vessel, body cavity or body duct.

If it would turn out during the ablation treatment that further anesthetization is needed, the sheath device 2 is extracorporeally snapped or clamped onto the fiber body 7 via the gap of the slotted opening 5. Thereafter the sheath device 2 and the injection means 9 are reintroduced, via the introducer sheath 15, into the blood vessel, the body cavity or the body duct, and is sliding over the fiber body 7, wherein the anesthetization step then is repeated to a desired extent. The possibility of such an easy and quick reassembly of the sheath device 2 and the fiber body 7 by use of the slotted opening 5 is a substantial advantage of the present invention and makes additional laborious measures from the operator, jeopardizing the whole ablation process, superfluous.

The proximal end 4 of the sheath device 2 also protrudes extracorporeally through the introducer sheath 15 constituting the inlet port in the skin 16 to the blood vessel, the body cavity or the body duct. As disclosed above, the withdrawal of the sheath device 2 and the injection means 9 located in the second bore 8 takes place incrementally between each injection step, and the operator may from the outside withdraw the sheath device 2 and the injection means 9 in a controlled way. The accuracy of the withdrawal can be determined by extracorporeal ultrasound guidance in a conventional way. Furthermore, and also as disclosed above, during the withdrawal of the sheath device 2 and the injection means 9, these can be rotated in the horizontal plane at a certain angle with a view to avoiding uneven anesthetization of the blood vessel, the body cavity or the body duct to be anesthetized. In the end of the ablation process the introducer sheath 15 is also withdrawn from the vein 1, wherein the parts of the inner surfaces of the vein 1 which have been covered by the introducer sheath 15 now become free and available, and are then subjected to the ablation treatment with the fiber body 7 until also these inner surfaces have been treated. Thereafter, the ablation process is fully completed, and the fiber body 7 is withdrawn from the patient, followed by covering the opening in the patient's skin.

The medical device and the kit according to the present invention may be used in connection with treatment of defective blood vessels, body cavities, and body ducts, which in one or another way are subject to a pathological, dysfunctional or abnormal condition. Examples of defective blood vessels are primarily veins, in particular insufficient superficial vein trunks causing varicose veins. Arteries may also be subjected to the method of ablation treatment according to the present invention. Examples of defect body cavities are cysts, fistulas, and tumors. Examples of defect body ducts which may be subjected to the method of ablation treatment according to the present invention are the bronchi, the bile duct, the urinary tract, and the gastrointestinal tract. In a preferred embodiment, which is represented in the Figures, the medical device and the kit according to the present invention are used in connection with treatment of varicose veins caused by insufficient superficial vein trunks.

With the medical device according to the present invention it is possible to inject and deposit any medical fluid in the tissue surrounding said defective blood vessels, body cavities, and body ducts. The medical fluid to be injected in connection with the method according to the present invention may be any one which may be useful in ablation treatment of defective blood vessels, body cavities, body ducts, and tumors, wherein an anesthetization step also is involved, but also for other purposes than ablation. In one embodiment the medical fluid is a conventional tumescent fluid having the ability to create intentional swelling, or tumescense, of a body tissue. In one embodiment the medical fluid is a conventional tumescent fluid and a conventional anesthetization fluid at the same time, i.e. having both a tumescent and an anesthetization action at the same time. An example of a tumescent fluid not being an anesthetization fluid is a sodium chloride solution. An example of an anesthetization fluid not being a tumescent fluid at the same time is carbocaine. An example of a tumescent fluid also being an anesthetization fluid at the same time is a mixed solution of sodium chloride and carbocaine. In one embodiment the medical fluid could be any cytostatic drug used for treating cancer tumors, wherein said cytostatic drug is injected in said surrounding tissue. In one embodiment the medical fluid is a sclerosant fluid used for destruction of undesired tissue, wherein said sclerosant fluid is injected in said surrounding tissue, causing destruction of said tissue. Although the invention has been disclosed with reference to the drawings for ablation treatment of varicose veins, the treatment of the other medical applications disclosed here may be performed by using the medical device, the kit and the method steps in a similar way, optionally without the fiber body 7.

While the invention has been described with reference to a number of embodiments, it will be understood by those skilled in the art that various changes may be made and equivalents may be substituted for elements thereof without departing from the scope of the present invention. In addition, many modifications may be made to adapt a particular situation or material to the teachings of the invention without departing from the essential scope thereof. Therefore, it is intended that the invention not be limited to the particular embodiments disclosed as the best mode contemplated for carrying out this invention, but that the invention will include all embodiments falling within the scope of the appended claims.

The invention claimed is:

1. A medical device to be inserted in a defective blood vessel, body cavity, or body duct for treatment thereof, comprising:

an essentially cylindrically formed elongated resilient sheath device having a distal end and a proximal end, wherein the distal end is fabricated from a body compatible metal material;

a slotted opening provided in the circumferential surface of the sheath device and extending in an axial direction;

a first bore provided in the sheath device and extending in the axial direction, the first bore having connection with the slotted opening, wherein the first bore is adapted to house an elongated fiber body, such that the sheath device is providing a clamping force around a major part of a perimeter of the fiber body;

and a second bore provided in the sheath device and extending in the axial direction, wherein the second bore is adapted to house an injection device, and wherein at least a portion of an inner surface of the second bore is fabricated from the body compatible metal material.

2. The medical device according to claim 1, wherein the sheath device is of an integral, one-piece construction and is made of a body compatible polymer material.

3. The medical device according to claim 1, wherein the sheath device has an outer cross-section diameter of 1.27-10.82 mm.

4. The medical device according to claim 1, wherein the second bore has a diameter sufficient to house an injection device having an outer diameter of 0.90-0.71 mm; and
wherein the cross-sectional area of the second bore is circular or oval.

5. The medical device according to claim 1, wherein the first bore has a circular cross-section.

6. The medical device according to claim 5, wherein the first bore has a diameter of 0.96-2.70 mm.

7. The medical device according to claim 1, wherein a gap between edges of the sheath device facing each other in the slotted opening is at most 1.3 mm.

8. The medical device according to claim 1, wherein the first bore is located between the slotted opening and the second bore.

9. The medical device according to claim 1, wherein the distance between the first bore and the second bore is at most 0.5 mm.

10. A kit for the treatment of defective blood vessels, body cavities, and body ducts, the kit comprising:
a medical device according to claim 1;
the fiber body to be received by the first bore; and
the injection device to be received by the second bore.

11. The kit according to claim 10, further comprising:
a container for a medical fluid; and
a regulation means for the administration of the medical fluid to the injection device; and
a generator of laser energy or radiofrequency energy.

12. The kit according to claim 10, wherein the first bore is adapted to house the fiber body and to allow a sliding action in the axial direction between the inner surface of the first bore and the circumferential surface of the fiber body.

13. The kit according to claim 10, wherein the fiber body is a fiber emitting laser energy or radiofrequency energy.

14. The kit according to claim 10, wherein the injection device is an injection needle having a distal tip;
wherein when the injection needle is extended out from the second bore, the distal tip deviates a predetermined distance in the radial direction.

15. The kit according to claim 14, wherein the injection needle is manufactured of a metal having memory properties.

16. The kit according to claim 10, wherein the second bore is adapted to house the injection device therein and to allow a sliding action in the axial direction between the inner surface of the second bore and the circumferential surface of the injection device.

17. The kit according to claim 11, wherein the container for the medical fluid contains a fluid having both tumescent and anesthetizing activity, a cytostatic activity, or a sclerosant activity.

18. The kit according to claim 11, further comprising:
an introduction sheath; and
a pump for forcing the medical fluid.

19. The medical device according to claim 1 for use in treatment of defective blood vessels, body cavities, or body ducts, wherein the defective blood vessels are veins or arteries:
wherein the defective body cavities are cysts, fistulas, and tumors; and
wherein the defective body ducts are the bronchi, the bile duct, the urinary tract, and the gastrointestinal tract.

20. A method for ablation treatment of defective blood vessels, body cavities, and body ducts, or for the deposition of a medical fluid in the tissue surrounding defective blood vessels, body cavities, and body ducts, the method comprising:
a) inserting the medical device according to claim 1, the fiber body, and the injection device into the lumen of a blood vessel, body cavity, or body duct until a predetermined location is reached, wherein the fiber body is inserted via the first bore and the injection device is inserted via the second bore;
b) pressing the injection device out from the second bore, wherein a needle tip of the injection device deviates in a radial direction, passes through the wall of the blood vessel, body cavity, or body duct, and reaches a perivascular tissue or a surrounding tissue;
c) injecting a medical fluid into the perivascular tissue or the surrounding tissue;
d) withdrawing the injection device back into the second bore;
e) withdrawing the sheath device and the injection device in a proximal direction until a new predetermined injection site has been reached, wherein the fiber body is not withdrawn;
f) repeating b)-e) until the walls of the blood vessel, body cavity, or body duct and the perivascular tissue or the surrounding tissue along the whole part of the blood vessel, body cavity, or body duct have been anesthetized;
g) removing the sheath device and the injection device, from the lumen of the blood vessel, body cavity, or body duct;
h) performing the ablation treatment of the inner walls of the blood vessel, body cavity, or body duct using the fiber body, wherein the fiber body is incrementally withdrawn in the proximal direction in the lumen until the whole part of the inner wall surface of the blood vessel, body cavity, or body duct to be treated has been subjected to the ablation treatment; and
i) withdrawing the fiber body from the lumen of the blood vessel, body cavity, or body duct, wherein the medical fluid has a tumescent and/or anesthetizing activity.

21. The method according to claim 20, wherein when during the step h) the injection step needs to be repeated, the sheath device is extracorporeally clamped around the fiber body and reintroduced into the blood vessel, body cavity, or body duct together with the injection device located in the second bore until the location of the injection has been reached, wherein the injection steps according to b)-d) are repeated one or more times.

22. The method according to claim 20, wherein the defective blood vessels are veins or arteries;
wherein the defective body cavities are cysts, fistulas, and tumors; and
wherein the defective body ducts are the bronchi, the bile duct, the urinary tract, and the gastrointestinal tract.

* * * * *